United States Patent [19]
Arakawa et al.

[11] Patent Number: 5,505,711
[45] Date of Patent: Apr. 9, 1996

[54] INDWELLING INJECTOR NEEDLE ASSEMBLY HAVING WINGS

[75] Inventors: Kuranosuke Arakawa, Sakai; Kazuhiro Shimizu, Shiga, both of Japan

[73] Assignee: Nissho Corporation, Osaka, Japan

[21] Appl. No.: 374,436

[22] Filed: Jan. 19, 1995

[30] Foreign Application Priority Data

Jan. 21, 1994 [JP] Japan ................................. 6-022075

[51] Int. Cl.⁶ ............................................. A61M 5/00
[52] U.S. Cl. ............................................. 604/171; 604/177
[58] Field of Search ............................ 604/171, 177, 604/198, 158, 263, 192, 164, 165

[56] References Cited

U.S. PATENT DOCUMENTS

| 5,120,320 | 6/1992 | Fayngold | 604/177 |
| 5,266,072 | 11/1993 | Utterberg et al. | 604/177 |
| 5,330,438 | 7/1994 | Gollobin et al. | 604/177 |
| 5,350,368 | 9/1994 | Shields | 604/177 X |
| 5,382,240 | 1/1995 | Lam | 604/171 X |

FOREIGN PATENT DOCUMENTS

| 0339812A2 | 11/1989 | European Pat. Off. . |
| 0550949A1 | 7/1993 | European Pat. Off. . |
| 0566769A1 | 10/1993 | European Pat. Off. . |
| 9311765U1 | 12/1993 | Germany . |
| 1-212561A | 8/1989 | Japan . |
| 6-7861B2 | 2/1994 | Japan . |

*Primary Examiner*—John D. Yasko
*Attorney, Agent, or Firm*—Ronald J. Kubovcik

[57] ABSTRACT

An indwelling injector needle assembly having wings includes a cannula or needle body, a hub supporting a proximal end of the needle body, a tube in fluid communication with the needle body, a cylindrical holder having a distal end from which the wings protrude, and a latching mechanism. The hub can slide along an inner periphery of the holder between a first position near the distal end of the holder and a second position near a proximal end of the holder. The latching mechanism is formed in and disposed between the hub and the holder so that the hub is inhibited from moving from the first position toward the second position, and vice versa. The needle edge can be retracted within the holder while its wings remain fixed to a patient's skin.

6 Claims, 4 Drawing Sheets

INDWELLING INJECTOR NEEDLE ASSEMBLY HAVING WINGS

BACKGROUND OF THE INVENTION

1. Field of the Invention

The present invention relates to the so-called indwelling injector needle having wings and a needle body and, more particularly, to an injector needle held in a protector having wings such that when the needle body slides into the protector after use, the needle edge is automatically retracted therein to protect a user from erroneously piercing his or her skin with the edge.

2. Description of the Prior Art

Conventional medical needles are usually separable from protective members designed to accommodate the needles. Users of those medical needles often have erroneously pricked their fingers with the edges of used needles, when the latter were restored in the protectors held by their fingers. Thus, there is and has been a possibility that the users might be infected with acquired immune deficiency syndrome (AIDS) or hepatitis. Some injector assemblies have been proposed or provided to prevent such accidents. For example, U.S. Pat. No. 5,120,320 discloses an injector assembly that comprises a protector integrally connected to an indwelling needle which has wing-shaped members. In this assembly a used needle is allowed to slide backward into the protector along a pair of guide slits formed longitudinally thereof so that the used needle's edge is hidden in the protector. In another assembly shown in Japanese Unexamined Patent Publication No. 1-212561, an indwelling needle is combined with a protector having wings. Due to a positioning mechanism intervening between the needle and the protector, the protector can slide toward the needle so that the needle edge is enclosed so as not to injure the user.

The wings integral with the needle body shown in U.S. Pat. No. 5,120,320 are secured to a patient's skin by means of adhesive tape or the like. Such an indwelling needle cannot be retracted in situ into the protector, unless the tape is torn off and the needle is withdrawn from the patient's skin. Further, the needle body shown in Japanese Unexamined Patent Publication No. 1-212561 often moves backward relative to the protector, due to the resistance of the skin being pricked with the needle. In addition, the needle body tends to slip off, when it is manually pulled backward to retract the needle edge into the protector.

SUMMARY OF THE INVENTION

Therefore, an object of the present invention is to provide an indwelling injector needle assembly which comprises a needle body operable to slide back into a protector having wings so that a needle edge can be retained securely in the protector. Another object is to provide a needle assembly designed such that a needle edge can be retracted into a protector while its wings remain fixed to a patient's skin.

In accordance with the objects of the invention, the indwelling injector needle assembly having wings of the invention includes a needle body in fluid communication with a tube. A hub is disposed on and supports the needle body. The hub has a guide groove and an auxiliary groove formed in a peripheral wall thereof, the grooves being located side by side and extending longitudinally of the hub. The auxiliary groove has a distal end terminating at a distal end of the hub and a proximal end in communication with the guide groove. A cylindrical holder having wings protruding therefrom is disposed on the hub. The holder has a lug protruding inwardly from an inner peripheral surface of a proximal end thereof. The lug is slidably engaged with the guide groove in the hub so that the hub can be moved relative to the holder between a first position in which the needle body protrudes from a distal end of the holder and a second position in which the needle body is retracted so that a pricking edge of the needle body is within the holder. The assembly also includes a latching mechanism for inhibiting the hub from being displaced from the first position toward the second position, and vice versa.

The latching mechanism may include a first locking means for holding the hub at the first position, and a second locking means for holding the hub at the second position. It will be apparent from FIGS. 3 and 4 and from the description given hereinafter that the first and second locking means are disposed at different angular positions around the axis of the hub. The members constituting the locking means will be detailed below.

When a patient's skin is pricked with the needle edge, the needle body will be at its first position relative to the cylindrical holder. The latching mechanism is effective to retain the needle hub in this position securely lest the resistance of the skin being pricked will displace the hub toward the second position, that is towards its proximal end. After a medical treatment using this assembly is completed, the cannula (the needle body) will be retracted into the holder to take the second position in which the needle edge is hidden within the holder. The latching mechanism also serves to inhibit the hub from moving toward the first position, that is towards its distal end, unless forcibly urged. Further, the needle hub is also prevented from moving backward beyond its second position, so that the needle body will never slip off the holder.

DESCRIPTION OF THE PREFERRED EMBODIMENTS

Figure 1:
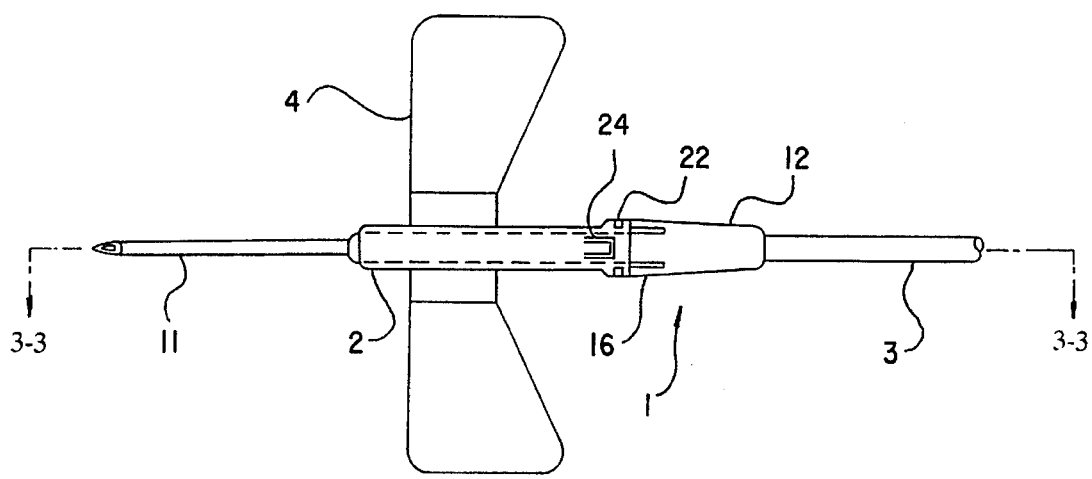
FIG. 1 is a plan view of a first embodiment of an injector needle assembly having wings.
Figure 2:
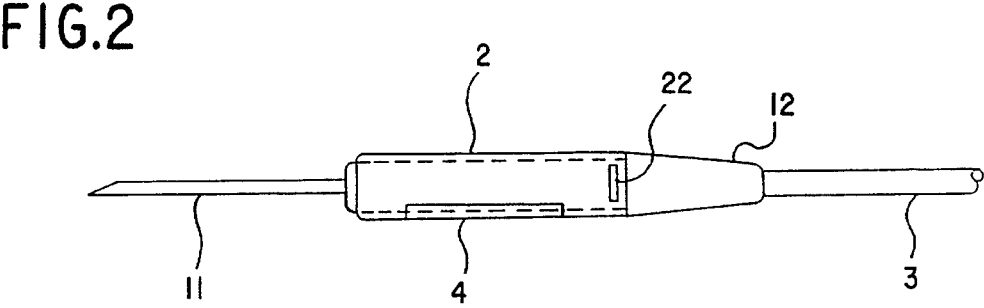
FIG. 2 is a front elevation of the assembly shown in FIG. 1.
Figure 3:
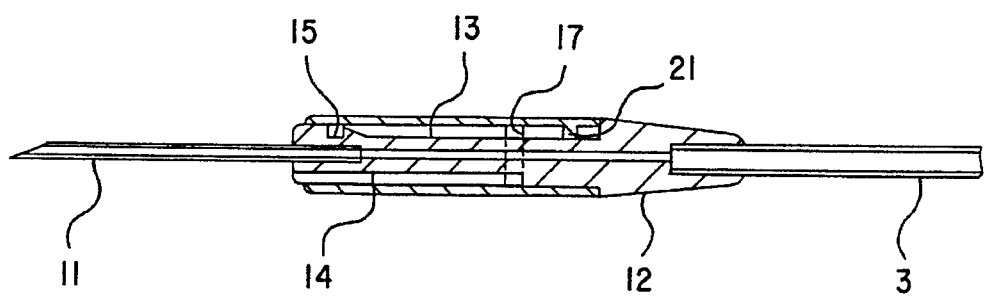
FIG. 3 is a cross section taken along line 3—3 in FIG. 1.

Embodiments of the present invention will now be described with reference to the drawings.

As shown in FIGS. 1–8, an injector needle assembly having wings provided in a first embodiment comprises a needle 1 having a tube 3 connected thereto, and a cylindrical holder 2 having wings 4 integral therewith. The needle 1 is slidable within the holder 2 between a first position where the needle protrudes forward a distance from a distal end of the holder and a second position where the needle is retracted into the holder. A latching mechanism is provided in and between a hub 12 of the needle 1 and the holder, in a manner such that the needle is inhibited from being displaced from the first position toward the second position, or vice versa. A guide groove 13 and an auxiliary groove 14 are formed in a peripheral wall of the hub 12, and located side by side and longitudinally of the hub. A distal end of the auxiliary groove 14 extends to and opens at a distal end of the holder 2, and a proximal end of the auxiliary groove communicates with the guide groove 13. A lug 21 is integral with an inner periphery of a proximal end of the holder 2. This lug 21 engages with and is slidable fore and aft in the guide groove 13.

Figure 4:
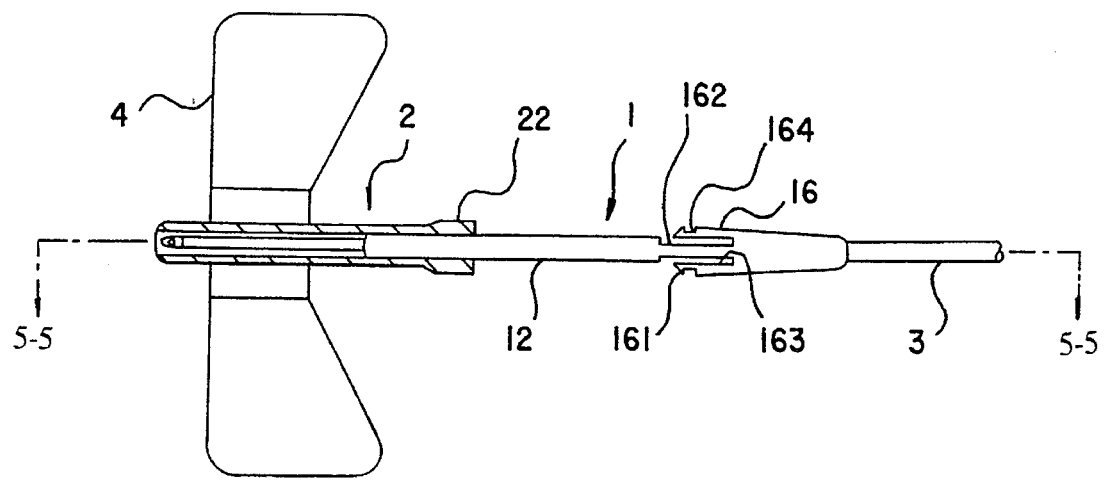
FIG. 4 is a plan view of the assembly shown in FIG. 1 and partly in cross section, with the needle end of the assembly being retracted within the holder.
Figure 5:
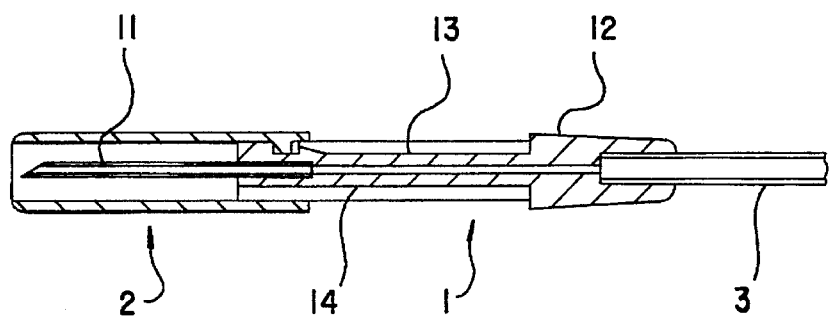
FIG. 5 is a cross section taken along the line 5—5—5—5 in FIG. 4.
Figure 8:
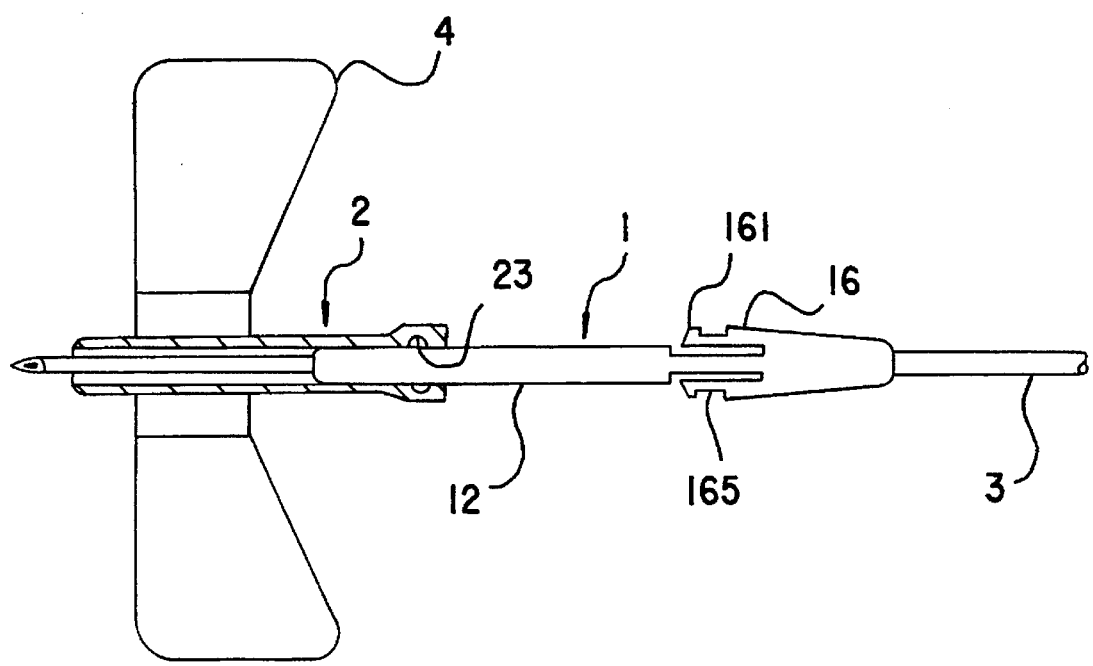
FIG. 8 is a plan view of a second embodiment of an injector needle having wings and shown partly in cross section.

A cannula 11, i.e, the hollow main body of the injector needle 1 is made, for example, of a metal such as stainless steel (preferably SUS-304) and has at its distal end a pricking edge. The proximal end of the cannula is connected to and held by a distal end of the hub 12. This hub 12, which has guide groove 13 and auxiliary groove 14 formed therein, is usually made of a flexible resin such as polypropylene, polyester, or polyethylene. The distal end of the auxiliary groove 14 extends to and opens at the distal end of the holder 2, and the proximal end of the auxiliary groove communicates with the guide groove 13. The distal closed end of the guide groove 13 is formed as a recess 15, and this groove 13 extends therefrom toward its proximal end. The recess 15 will engage with the lug 21 of the holder 2, when the needle 1 is retracted to the second position relative to the holder 2. A tube 3 is connected to the proximal end of the hub 12, which usually has two arms 16 disposed symmetrically and side by side. Alternatively, only one such arm may suffice. Each arm 16, which extends forwardly toward the distal end of the hub from a proximal end portion thereof so as to be disposed behind the guide groove 13, may be shaped as shown in FIG. 4. Hook 161 is integrally formed on a distal end of arm 16 and a slit 163 intervenes between each arm and a central columnar portion 162. Slits 163 allow the arms to flex easily and inwardly, because the hub 12 is made of a flexible material as described above. Each hook 161 has a generally U-shaped recess 164 as shown in FIGS. 1 and 4. The hook is engageable with an aperture 22 and disengageable therefrom by flexing the arms 16 toward each other. Alternatively, each arm 16 may have a distal end having a spherically convex shape (as shown in FIG. 8) protruding outwardly of the hub so that a thin portion 165 is provided between the distal end and a proximal end of each arm. In this case, each hook 161 may readily be disengaged from a corresponding shallow recess 23 formed in the proximal end of the holder 2, by simply pulling the hub 12 away from the holder. The number of apertures 22 or recesses 23 preferably is the same as the number of arms 16.

Figure 6:
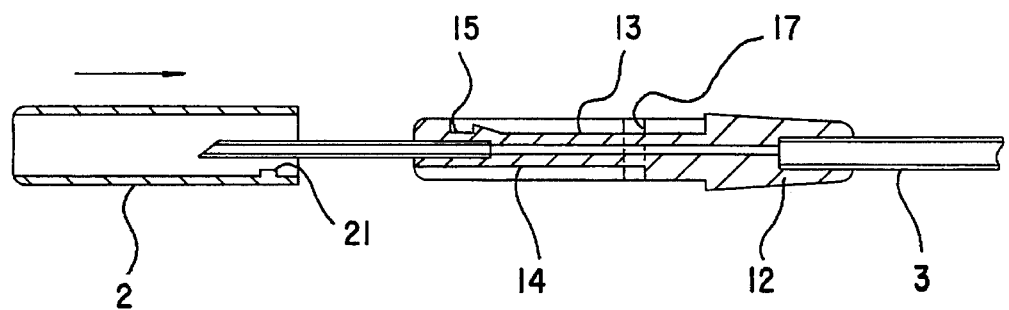
FIG. 6 illustrates the first step of forming the assembly.
Figure 7:
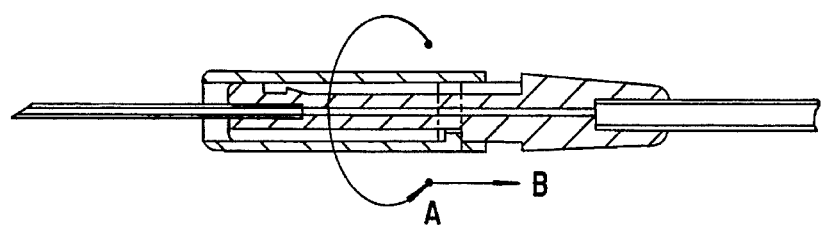
FIG. 7 illustrates the succeeding step of forming the assembly.

The auxiliary groove 14, useful when assembling this injector needle unit, extends to and opens forwardly at the distal end of the hub 12, lest the lug 21 formed at the proximal end of the cylindrical holder 2 should hinder the hub from being inserted therein. As a result of this feature, the lug 21 is allowed to slide along the auxiliary groove 14, until the hub is completely received in the holder 2. The lug 21 will then be transferred into the guide groove 13, because the latter communicates with the auxiliary groove. The first step of assembling this injector needle unit having wings is shown in FIG. 6. In this step, the lug 21 of the holder 2 will be caused to slide in and along the auxiliary groove 14 until bearing against the proximal end thereof so that the hub 12 is fully inserted in the holder, as will be apparent. In the next step, the holder 2 will then be rotated in the direction indicated at the arrow in FIG. 7. The lug 21 will thus transfer from the auxiliary groove 14 to the guide groove 13 communicating therewith through a transverse passage 17. Thereafter, the cylindrical holder 2 will be moved toward its proximal end so that its lug 21 now slides in the guide groove 13, until abutting the proximal end thereof and simultaneously causing each arm's hook 161 of the hub to fit in the corresponding aperture 22.

The holder 2 is a cylindrical member for accommodating the hub 12, and the wings 4 integrally protruding sideways from the distal end portion of the holder are flexible. The hub 12 is slidable within the holder and along an inner periphery thereof, between the first position and the second position. As described above, the cannula will protrude a distance from the distal end of the holder 2 at the first position, whereas the cannula is retracted within the holder 2 at the second position. The lug 21 engageable with the recess 15 formed in the hub 12 protrudes inwardly from the inner periphery of the proximal end portion of the holder, as shown in FIGS. 3 and 5 to 7. The lug 21 fitted in the guide groove 13 of the hub 12 is slidable only between the proximal and distal ends of the groove. Each aperture 22 engageable with the corresponding arm's hook 161 is formed through a portion of the peripheral wall of the holder, this portion being located nearer the proximal end of holder than the lug 21. In the case in which the hook 161 comprises a spherically convex end as shown in FIG. 8, the shallow recesses 23 may substitute for the apertures 22, at the same holder portions as the latter are located. The reference numeral 24 denotes a slit that facilitates the outward flexing of the holder portion where the lug 21 is formed. Such a slit will help this lug smoothly enter the auxiliary groove 14 and smoothly travel along the guide groove 13.

In use, the hub 12 of the described needle assembly having wings will take an indwelling position relative to the holder 2 as shown in FIG. 1. This position is the first position described above, in which the cannula's distal end protrudes from the holder 2 and the arms 16 (viz. their hooks 161) are in engagement with the respective apertures 22 (or shallow recesses 23). Arms 16 and apertures 22 (or recesses 23) constitute the first latching means which prevents the hub 12 from moving relative to and toward the proximal end of the holder 2, when pricking the patient's skin with the needle edge.

After use, the user grips the arms 16 of the injector needle assembly shown in FIG. 1 with his or her fingers so that the arms flex inwards so as to be disengaged from the apertures 22. While gripping the arms, the user will then move the hub 12 rearwardly toward its proximal end. The lug 21 of the cylindrical holder is displaced in this manner along the guide groove 13, from the first position to the second position, until engaging with the recess 15 located at the distal end of the groove. Thus, the lug 21 cooperates with the recess 15 to provide the second locking means for this injector needle assembly. The hub is thus locked at the second position where the pricking edge of cannula 11 is completely retracted within the holder. If the assembly is of a modified structure as shown in FIG. 8, then the arms 16 will likewise be gripped first. However, the simple backward pulling of the hub 12 will cause the hooks 161 to flex inwards so that the lug 21 disengages from the shallow recess 23. This motion will similarly be followed by the displacement of the lug from the first position to the second position in which the hub is locked by the lug 21 engaging with the recess 15 and the pricking edge of cannula 11 is completely retracted within the holder.

It will now be apparent that the injector needle assembly having wings and provided herein is effective to protect those who are engaged in medical treatments and/or operations from erroneously pricking their skin with needle edges. It is further advantageous that the present assembly whose hub need only be displaced within the cylindrical holder toward the proximal end thereof to enclose the needle edge can be used more easily than the prior art assemblies whose wings have to be removed before removing the needle bodies.

What is claimed is:

1. An indwelling injector needle assembly having wings, said assembly comprising:

a needle body in fluid communication with a tube;

a hub disposed on and supporting said needle body, said hub having a guide groove and an auxiliary groove formed in a peripheral wall thereof, said grooves being located side by side and extending longitudinally of said hub, said auxiliary groove having a distal end terminating at a distal end of said hub and a proximal end in communication with said guide groove;

a cylindrical holder disposed on said hub, said holder having wings protruding therefrom and a lug protruding inwardly from an inner peripheral surface of a proximal end thereof, said lug being slidably engaged with said guide groove in said hub so that said hub can be moved relative to said holder between a first position in which said needle body protrudes from a distal end of said holder and a second position in which said needle body is retracted so that a pricking edge of said needle body is within said holder; and a latching mechanism for inhibiting said hub from being displaced from said first position toward said second position, and vice versa.

2. The indwelling injector needle assembly of claim 1, wherein the latching mechanism comprises a first locking means for holding the hub at the first position, and a second locking means for holding the hub at the second position.

3. The indwelling injector needle assembly of claim 2, wherein the first locking means comprises at least one arm and at least one aperture, said arm being integral with the hub and being disposed at a proximal end of the guide groove, said aperture being formed through a peripheral wall of the holder and being disposed at a proximal end of the lug, and wherein said arm has a hook for engaging said aperture and integrally formed on a distal and outer end of said arm, said hook being capable of being disengaged from said aperture by flexing said arm.

4. The indwelling injector needle assembly of claim 2, wherein the first locking means comprises at least one arm and at least one shallow recess, said arm being integral with the hub and being disposed at a proximal end of the guide groove, said arm having an outwardly protruding convex end for engaging said shallow recess and integrally formed on a distal and outer surface of said arm, said shallow recess being formed in a peripheral wall of the holder and being disposed at a proximal end of the lug, and wherein said convex end is disengaged from said shallow recess by pulling the hub away from the holder.

5. The indwelling injector needle assembly of claim 3, wherein the second locking means comprises the lug of the holder and a recess formed in the guide groove of the hub at a distal end of the guide groove, the lug engaging with said recess when the hub is moved from the first position to the second position.

6. The indwelling injector needle assembly of claim 4, wherein the second locking means comprises the lug of the holder and a recess formed in the guide groove of the hub at a distal end of the guide groove, the lug engaging with said recess when the hub is moved from the first position to the second position.

* * * * *